(12) United States Patent  
Haralambidis

(10) Patent No.: US 11,801,396 B1
(45) Date of Patent: Oct. 31, 2023

(54) WEARABLE DEVICE INCLUDING UVC LIGHT SOURCE FOR REDUCTION IN VIRUS AND BACTERIA TRANSMISSION

(71) Applicant: Cosmo Haralambidis, Cranston, RI (US)

(72) Inventor: Cosmo Haralambidis, Cranston, RI (US)

( * ) Notice: Subject to any disclaimer, the term of this patent is extended or adjusted under 35 U.S.C. 154(b) by 33 days.

(21) Appl. No.: 17/190,467

(22) Filed: Mar. 3, 2021

Related U.S. Application Data

(60) Provisional application No. 62/987,733, filed on Mar. 10, 2020.

(51) Int. Cl.
*A61N 5/06* (2006.01)

(52) U.S. Cl.
CPC .... *A61N 5/0624* (2013.01); *A61N 2005/0647* (2013.01); *A61N 2005/0661* (2013.01)

(58) Field of Classification Search
CPC .......... A61N 5/0624; A61N 2005/0647; A61N 2005/0661; A61N 5/06–2005/073
See application file for complete search history.

(56) References Cited

U.S. PATENT DOCUMENTS

| | | | |
|---|---|---|---|
| 1,554,682 A | 9/1925 | Merke | |
| 4,464,336 A | 8/1984 | Hiramoto | |
| 5,165,395 A | 11/1992 | Ricci | |
| 5,683,436 A * | 11/1997 | Mendes | A61N 5/0603 607/90 |
| 6,443,978 B1 | 9/2002 | Zharov | |
| 6,461,568 B1 | 10/2002 | Eckhardt | |
| 6,523,179 B1 | 2/2003 | Zegarelli et al. | |
| 6,901,930 B2 | 6/2005 | Henley | |
| 7,392,806 B2 | 7/2008 | Yuen et al. | |
| 7,506,992 B2 | 3/2009 | Carter | |
| 8,001,968 B2 | 8/2011 | Doty et al. | |
| 8,733,356 B1 * | 5/2014 | Roth | A62B 18/003 128/205.27 |
| 9,402,433 B2 | 8/2016 | York | |
| 10,071,262 B2 | 9/2018 | Randers-Pehrson et al. | |
| 10,180,249 B2 | 1/2019 | Murphy et al. | |
| 10,240,771 B2 | 3/2019 | Murphy et al. | |
| 10,335,618 B2 | 7/2019 | Zhou et al. | |
| 10,589,119 B2 * | 3/2020 | Kim | A61N 5/06 |
| 10,780,189 B2 * | 9/2020 | Randers-Pehrson | A61L 2/26 |
| 10,835,410 B2 * | 11/2020 | Jafarzadeh | A61N 5/0625 |

(Continued)

FOREIGN PATENT DOCUMENTS

| | | |
|---|---|---|
| EP | 1991904 A1 | 11/2008 |
| EP | 2465543 B1 | 5/2013 |

(Continued)

OTHER PUBLICATIONS

Ushio America, Inc., "Care222®, Handheld Device" product brochure, Form No. S-CARE222-HH/0120, 2020, 1 Page.

(Continued)

*Primary Examiner* — Jonathan T Kuo

(57) ABSTRACT

A wearable device includes a support structure wearable by an individual and a UVC light source mounted on the support structure. When the support structure is worn by the individual the UVC light source is directed at oral and nasal cavities of the individual. The wearable device can be eyeglasses.

20 Claims, 2 Drawing Sheets

(56) References Cited

U.S. PATENT DOCUMENTS

| | | | |
|---|---|---|---|
| 2003/0018373 | A1 | 1/2003 | Eckhardt et al. |
| 2004/0216745 | A1 | 11/2004 | Yuen et al. |
| 2007/0195259 | A1 | 8/2007 | Olsson |
| 2008/0232092 | A1 | 9/2008 | Carter |
| 2009/0004047 | A1 | 1/2009 | Hunter et al. |
| 2009/0204185 | A1 | 8/2009 | De et al. |
| 2010/0222852 | A1* | 9/2010 | Vasily .................. A61N 5/0616 607/88 |
| 2012/0279503 | A1 | 11/2012 | Zhou et al. |
| 2013/0013032 | A1 | 1/2013 | Irwin |
| 2015/0335910 | A1* | 11/2015 | Tapper ................. A61N 5/0616 607/90 |
| 2017/0333727 | A1* | 11/2017 | Kim ......................... A61N 5/06 |
| 2018/0169279 | A1* | 6/2018 | Randers-Pehrson ...... A61L 2/10 |
| 2018/0280718 | A1* | 10/2018 | Tsubota ................... A61H 5/00 |
| 2018/0303654 | A1* | 10/2018 | Jafarzadeh ............... A61F 9/04 |
| 2019/0045782 | A1 | 2/2019 | Edye |
| 2020/0085984 | A1* | 3/2020 | Randers-Pehrson ........................ A61N 5/0624 |

FOREIGN PATENT DOCUMENTS

| | | |
|---|---|---|
| WO | 2020023778 A1 | 1/2020 |
| WO | 2021241034 A1 | 12/2021 |

OTHER PUBLICATIONS

Materion Corporation, "Combo-Lids™" product brochure, undated, circa 2020, 4 Pages.

Ushio America, Inc., "Care222, Excimer Lamps, FAR UV-C", Form B-0220, undated, circa 2020, 2 Pages.

Materion Corporation, "Combo-Lids™" data sheet, undated, circa 2020, 1 Page.

Crystal IS, Inc., "Crystal IS: Environmental Health and Safety for Crystal IS UVC Diodes", Application Note AN001, Apr. 23, 2014, 8 Pages.

Ushio America, Inc., "Care222®, Ceiling-Wall-Mount-Device" product brochure, Form No. S-CARE222-CM/0120, 2020, 2 Pages.

Yamada, Haruki, "Performance Test for Virus Inactivation Efficacy by UV Irradiation", Kitasato Research Center for Environmental Science, KRCES Report #2019_0032, Sep. 11, 2019, 8 Pages.

Multiple Anonymous Authors, "Looking for a Source of LEDs with Emission at 207 nm", CandlePowerForums, circa Mar. 2018, https://www.candlepowerforums.com/threads/looking-for-a-source-of-leds-with-emission-at-207-nm.444304, 4 Pages.

Materion Corporation, "Killing Germs With Leds: Materion UV-C Windows Aid Disinfection", 2020, 3 Pages.

Welch, et al., "Far-UVC light: A new tool to control the spread of airborne-mediated microbial diseases", Scientific Reports, Feb. 9, 2018, 7 Pages.

Materion Corporation, Advanced Materials Group, "Microelectronic Packaging Comparison Chart", undated, 1 Page.

European Commission, Scientific Committee on Consumer Products(SCCP), "Opinion on Biological effects of ultraviolet radiation relevant to health with particular reference to sunbeds for cosmetic purposes", SCCP Document SCCP/0949/05, Adopted by the SCCP during the 8th plenary of Jun. 20, 2006, Jun. 20, 2006, 43 Pages.

Ozog, et al., "The Effect of Ultraviolet C Radiation Against SARS-COV-2 Inoculated N95 Respirators", medRxiv preprint doi: https://www.medrxiv.org/content/10.1101/2020.05.31.20118588v3, Jun. 26, 2020, 21 Pages.

Downes, Arthur and T. P. Blunt, "The Influence of Light upon the Development of Bacteria", Nature, p. 218, Jul. 12, 1877, 1 Page.

Crystal IS, Inc., "What is UVC Light?: Ultraviolet (UV) Light is a Component of the Electromagnetic Spectrum that falls in the Region Between Visible Light and X-Rays", 2020, 8 Pages.

Underwriters Laboratories, "Ultraviolet-C (UVC) germicidal devices: what consumers need to know", form CT 26219573-0720, 2020, 2 Pages.

Underwriters Laboratories, "Ultraviolet-C (UVC) Germicidal Products Reference Guide", Form CS677192-0821, 2021, 3 Pages.

Stanford Solar Center, "UV Light", 2015, 3 Pages.

Materion Corporation, "Visi-Lid™ Optical Window Attached Etch Lid", undated, circa 2020, 2 Pages.

Buonanno, et al., "207-nm UV Light—A Promising Tool for Safe Low-Cost Reduction of Surgical Site Infections. I: In Vitro Studies", PLoS One | www.plosone.org, vol. 9, Issue 10, e76968., Oct. 2013, 7 Pages.

Buonanno, et al., "Germicidal Efficacy and Mammalian Skin Safety of 222-nm UV Light", BioOne Complete, Source Radiation Reearch, 187(4): 493-501, Published By: Radiation Research Society, URL: https://doi.org/10.1667/RR0010CC.1, Mar. 10, 2020, 10 Pages.

Kahn, Kevin, "Is UVC Safe?", undated, from https://klaran.jp/is-uvc-safe, 5 Pages.

Kang, et al., "Decontamination Effect of the Spindle and 222-Nanometer Krypton-Chlorine Excimer Lamp Combination Against Pathogens on Apples (*Malus domestica* Borkh.) and Bell Peppers (*Capsicum annuum* L.)", Applied and Environmental Microbiology, vol. 85, Issue 12, , Jun. 2019, 14 Pages.

Crist, Ry, "UVC wands kill viruses. Experts warn they're also a 'major safety issue'", CNET, available at https://www.cnet.com/home/smart-home/uvc-light-wands-kill-viruses-experts-warn-major-safety-issue-coronavirus-covid-19/, Oct. 20, 2020, 20 pages.

Altman, Andy, "Flying coronavirus-killer: How this drone fights COVID-19", CNET, available at https://www.cnet.com/science/flying-coronavirus-killer-how-this-drone-fights-covid-19/, Apr. 21, 2020, 2 pages.

Crist, Ry, "UV light and the coronavirus: Big Ass Fans might have a solution", CNET, available at https://www.cnet.com/home/smart-home/uv-light-and-the-coronavirus-big-ass-fans-might-have-a-solution-haiku-uvc-covid-19/, Aug. 8, 2020, 8 pages.

U.S. Food and Drug Administration, "UV Lights and Lamps: Ultraviolet-C Radiation, Disinfection, and Coronavirus", available at https://www.fda.gov/medical-devices/coronavirus-covid-19-and-medical-devices/uv-lights-and-lamps-ultraviolet-c-radiation-disinfection-and-coronavirus, Feb. 1, 2021, 3 pages.

\* cited by examiner

WEARABLE DEVICE INCLUDING UVC LIGHT SOURCE FOR REDUCTION IN VIRUS AND BACTERIA TRANSMISSION

CROSS-REFERENCE TO RELATED APPLICATION

This application claims priority to, and is a nonprovisional application of, prior filed U.S. Provisional Patent Application Ser. No. 62/987,733, filed Mar. 10, 2020, entitled "WEARABLE DEVICE INCLUDING UVC LIGHT SOURCE FOR REDUCTION IN VIRUS AND BACTERIA TRANSMISSION", which is hereby incorporated by reference.

SUMMARY

This Summary introduces a selection of concepts in simplified form that are described further below in the Detailed Description. This Summary neither identifies key or essential features, nor limits the scope, of the claimed subject matter.

UVC light has been proven to be effective against airborne virus and bacteria transmission. This light source also is very safe for human skin. Specifically, UVC light around the wavelength of about 222 nm+/−2 nm is both safe for direct exposure to human skin and tissue, including eyes and mucous membranes, while also being effective against single cell organisms, bacteria, and viruses.

A UVC light source can be mounted on a support structure wearable by an individual, such as a pair of eyeglasses. When the support structure is worn by the individual, and the UVC light source is on, UVC light is directed at oral and nasal cavities of the individual. For example, UVC light can be delivered from the bottom portion of the lens frame of a pair of eyeglasses with enough range of light to fully cover the mouth and nose area. With eyeglasses, the eye coverage will also prevent eye touching, which is the third mode of entry of virus or bacteria. Eyeglasses or other wearable device that can direct UVC light near the oral and nasal cavity and that can support the light source and a battery system for the light source can be used. Eyeglasses provide a fairly universal and easy to manufacture device, and are deliverable to all age ranges.

The following Detailed Description references the accompanying drawings which form a part this application, and which show, by way of illustration, specific example implementations. Other implementations may be made without departing from the scope of the disclosure.

DETAILED DESCRIPTION

Figure 1:
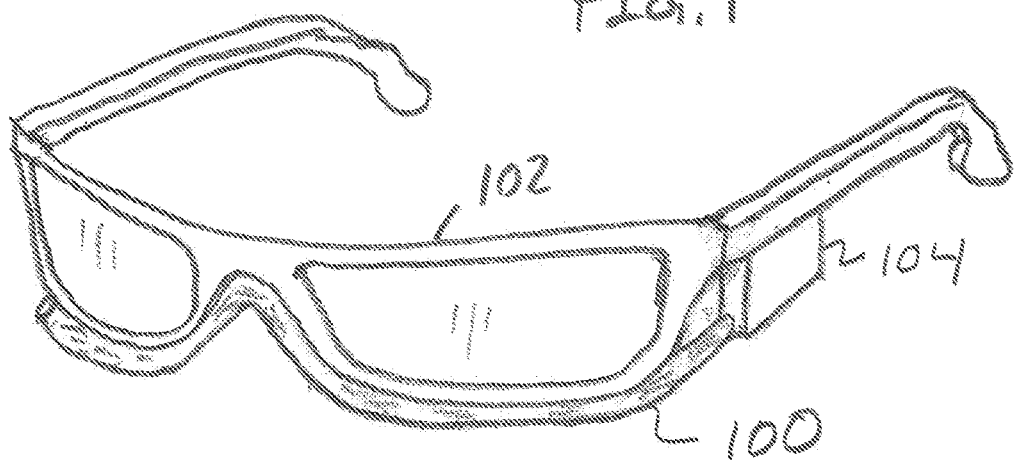
FIG. 1 is a perspective view of an example embodiment of a pair of eyeglasses incorporating a UVC light source.

FIG. 1 shows a perspective view of an example embodiment of a pair of eyeglasses incorporating a UVC light source. Other kinds of wearable devices that can direct UVC light near the oral and nasal cavity and that can support the light source and a battery system for the light source can be used. Generally, the wearable device will include a support structure wearable by an individual. A UVC light source is mounted on the support structure. The arrangement of the UVC light source on the support structure is such that when the support structure is worn by the individual, the UVC light source is directed at oral and nasal cavities of the individual.

The UVC light range, such as light with a 222 nm wavelength, has been shown to be safe for direct exposure to human skin and tissue. Such light affects single cell organisms, bacteria, and viruses. Using a wearable device with a UVC light source directed towards the nose and mouth area, airborne bacteria and viruses are reduced or killed prior to their entry into the nose or mouth. Constant light can reduce transmission in public. The wearable device can be removed and directed at another surface, typically for about 10 minutes, to eliminate or reduce existing bacteria or viruses on that surface.

Figure 2:
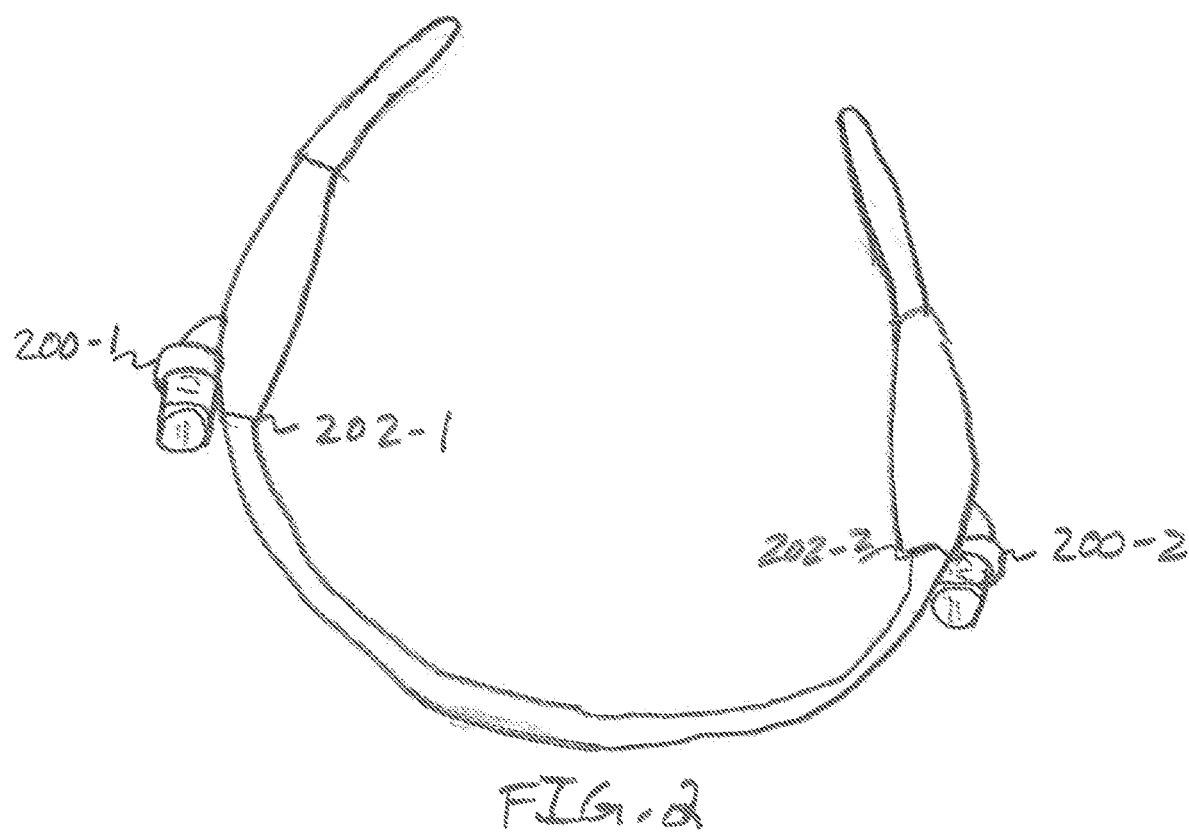
FIG. 2 is a top view of an example embodiment of a pair of eyeglasses incorporating a UVC light source.
Figure 3:
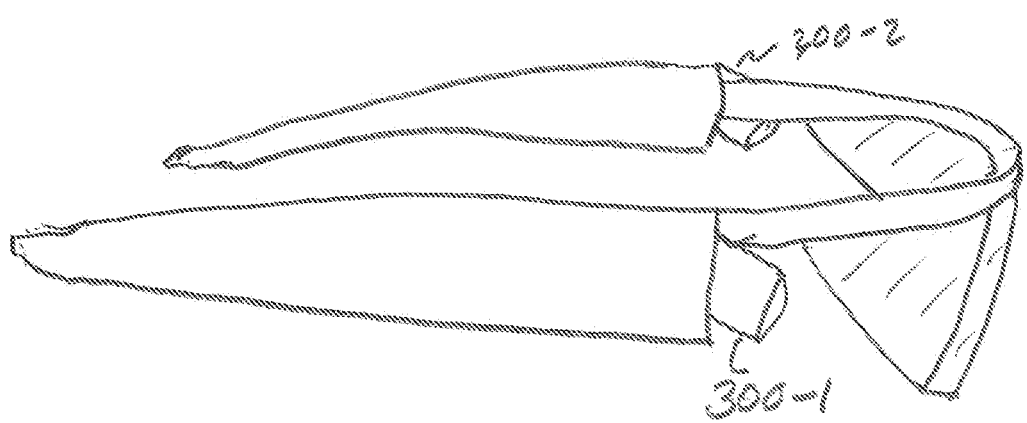
FIG. 3 is a side view of an example embodiment of the embodiment of FIG. 2.

As shown in FIGS. 1-3, the support structure can include the frame of a pair of eyeglasses. The eyeglasses do not need to be otherwise corrective eyewear (including prescription lenses) or protective eyewear (such as sunglasses or safety goggles), but can be a frame with transparent material over the eyes.

An optical fiber or glass or optical filter, or other material can transmit UVC light originating from a light source such as a light emitting diode (LED). A typical light source for providing UVC light, such as a lamp, produces light with a wavelength in the range of about 220-250 nm. A bandpass filter can be used in combination with a lamp to provide a narrow band of UVC light.

In the example implementation shown in FIG. 1, a UVC light source is implemented using an optical fiber 100 formed on a bottom portion of the lens frame 102 of a pair of eyeglasses with enough range of light to fully cover the mouth and nose area. The optical fiber is connected to receive UVC light from the output of a lamp filtered using a bandpass filter. The lamp and bandpass filter may be mounted on the glasses as indicated at 104 or may be in separate packaging connected to the glasses using fiber optics.

FIG. 2 is a top view of an example embodiment of a pair of eyeglasses incorporating a UVC light source. In the example implementation shown in FIG. 2, a UVC light source (200-1, 200-2) comprises a lamp and a bandpass filter, and is formed at the left and right edges (202-1, 202-2) of the lens frames of a pair of eyeglasses. FIG. 3 is a side view illustrating the light source directed towards the nose and mouth area.

In some implementations, a power source, such as a battery, and other control circuitry, such as a microprocessor, can be included in the side handle or arms of the eyeglasses, such as at 104 in FIG. 1. In some implementations, the power source and control circuitry can be externally supplied and connected to the eyeglasses through wires. In some implementations, wires with an appropriate adapter can connect to a mobile phone or other similar device to provide power and control.

As an example implementation, the UVC lamp can be a lamp that provides a range of wavelengths that includes at least a 222 nm wavelength of suitable amplitude. Such lamps can be, for example, deuterium lamps, xenon lamps, mercury xenon lamps, or hallow cathode lamps. A source of such lamps to generate UVC light include those manufactured by Hamamatsu Photonics, K.K. of Japan.

As an example implementation, the bandpass filter generally is any filter that can block out most non-UV wavelengths, let allow a range of UV light wavelengths to pass, typically with a center wavelength in the 210 nm to 225 nm range, and preferably closer to 222 nm and with as narrow a band as possible. An example commercially available filter is from Midwest Optical Systems, Inc., of Palatine, Illinois, and is called a bp250 filter, or other custom made filter from this manufacturer with a center wavelength closer to 222 nm, but with similar dimensions. For this filter, the physical size of the filter is about 3 mm to 4 mm (round or square). Other sources of filters include but are not limited to Andover Corporation of Salem, New Hampshire, and eSource Optics, of Whitinsville, Massachusetts, both of which have 222 nm bandpass filters in 12.5 mm sizes.

It should be understood that the subject matter defined in the appended claims is not necessarily limited to the specific implementations described above. The specific implementations described above are disclosed as examples only.

What is claimed is:

1. A wearable device comprising:
   a support structure wearable by an individual, wherein the support structure comprises a frame of eyeglasses; and
   a UVC light source mounted on the support structure, such that, when the support structure is worn by the individual, UVC light from the UVC light source is directed towards the nose and mouth area of the individual to affect virus and bacteria prior to entry of the virus and bacteria into the nose or mouth, wherein the UVC light has a center wavelength in a range of 210 nanometers to 225 nanometers.

2. The wearable device of claim 1, wherein the UVC light source comprises a UVC lamp that provides light in a range of wavelengths that includes at least a 222 nanometer wavelength, and a bandpass filter which blocks out non-UV wavelengths of the light from the UVC lamp so that the light is filtered to provide the UVC light in a band of wavelengths in the range of 222 nanometers+/−2 nanometers.

3. The wearable device of claim 2, further comprising an optical fiber formed on a bottom portion of a lens frame of the frame of eyeglasses and connected to receive the UVC light such that the UVC light from is delivered by the optical fiber from the bottom portion of the lens frame.

4. The wearable device of claim 3, wherein the UVC light is delivered by the optical fiber with a range of light that covers the mouth and nose area.

5. The wearable device of claim 3, wherein the UVC lamp and the bandpass filter are mounted on the frame of eyeglasses.

6. The wearable device of claim 3, wherein the UVC lamp and the bandpass filter are in packaging separate from the frame of eyeglasses and are connected to the frame of eyeglasses using fiber optics.

7. The wearable device of claim 3, wherein the transparent material comprises corrective eyewear.

8. The wearable device of claim 3, wherein the transparent material are protective eyewear.

9. The wearable device of claim 3, wherein the transparent material comprises prescription lenses.

10. The wearable device of claim 1, wherein the UVC light source comprises:
   a first UVC lamp that provides light in a range of wavelengths that includes at least a 222 nanometer wavelength, and a first bandpass filter which blocks out non-UV wavelengths of the light from the UVC lamp so that the light is filtered to provide the UVC light in a band of wavelengths in the range of 222 nanometers+/−2 nanometers; and
   a second UVC lamp that provides light in a range of wavelengths that includes at least a 222 nanometer wavelength, and a second bandpass filter which blocks out non-UV wavelengths of the light from the UVC lamp so that the light is filtered to provide the UVC light in a band of wavelengths in the range of 222 nanometers+/−2 nanometers.

11. The wearable device of claim 1, wherein the UVC light source comprises:
   a first UVC lamp that provides light in a range of wavelengths that includes at least a 222 nanometer wavelength, and a first bandpass filter which blocks out non-UV wavelengths of the light from the UVC lamp so that the light is filtered to provide a first portion of the UVC light in a band of wavelengths in the range of 222 nanometers+/−2 nanometers, wherein the first UVC lamp and the first bandpass filter are formed at a left edge of a lens frame of the frame of eyeglasses; and
   a second UVC lamp that provides light in a range of wavelengths that includes at least a 222 nanometer wavelength, and a second bandpass filter which blocks out non-UV wavelengths of the light from the UVC lamp so that the light is filtered to provide a second portion of the UFC light in a band of wavelengths in the range of 222 nanometers+/−2 nanometers, wherein the second UVC lamp and the second bandpass filter are formed at a right edge of a lens frame of the frame of eyeglasses.

12. The wearable device of claim 1, further comprising an optical fiber formed on a bottom portion of a lens frame of the frame of eyeglasses and connected to the UVC light source such that the UVC light from the UVC light source is delivered by the optical fiber from the bottom portion of the lens frame.

13. The wearable device of claim 12, wherein the UVC light from the UVC light source is delivered by the optical fiber with a range of light that covers the mouth and nose area.

14. The wearable device of claim 1, wherein the frame of eyeglasses comprises a lens frame supporting a transparent material placed over eyes of the individual when the frame of eyeglasses is worn by the individual.

15. The wearable device of claim 1, further comprising control circuitry included in the support structure.

16. The wearable device of claim 1, further comprising control circuitry connected to the support structure through wires.

17. The wearable device of claim 16, wherein a mobile phone provides power and the control circuitry.

18. A wearable device comprising:
   a UVC light source emitting UVC light having a center wavelength in a range of 210 nanometers to 225 nanometers; and
   a frame of eyeglasses configured to be worn on a face of an individual;
   wherein the UVC light source is mounted on the frame of eyeglasses, and wherein when the frame of eyeglasses is worn on the face by the individual, the UVC light source directs the UVC light towards the nose and mouth area of the individual to affect virus and bacteria prior to entry of the virus and bacteria into the nose or mouth of the individual.

19. The wearable device of claim 18, wherein the frame of eyeglasses comprises a lens frame supporting a transparent material placed over eyes of the individual when the frame of eyeglasses is worn by the individual.

20. The wearable device of claim 18, wherein the UVC light source comprises:

a first UVC lamp that provides light in a range of wavelengths that includes at least a 222 nanometer wavelength, and a first bandpass filter which filters out non-UV wavelengths of the light from the UVC lamp to provide a first portion of the UVC light in a band of wavelengths in the range of 222 nanometers+/−2 nanometers, wherein the first UVC lamp and the first bandpass filter are attached to a left edge of a lens frame of the frame of eyeglasses; and a second UVC lamp that provides light in a range of wavelengths that includes at least a 222 nanometer wavelength, and a second bandpass filter which filters out non-UV wavelengths of the light from the UVC lamp to provide a second portion of the UFC light in a band of wavelengths in the range of 222 nanometers+/−2 nanometers, wherein the second UVC lamp and the second bandpass filter are attached to a right edge of a lens frame of the frame of eyeglasses.

\* \* \* \* \*